US009693684B2

(12) United States Patent
Lopez et al.

(10) Patent No.: US 9,693,684 B2
(45) Date of Patent: Jul. 4, 2017

(54) SYSTEMS AND METHODS OF EYE TRACKING CALIBRATION

(71) Applicant: Facebook, Inc., Menlo Park, CA (US)

(72) Inventors: Javier San Agustin Lopez, Copenhagen S (DK); John Paulin Hansen, Roskilde (DK); Sebastian Sztuk, Copenhagen N. (DK); Martin Henrik Tall, Frederiksberg C. (DK)

(73) Assignee: Facebook, Inc., Menlo Park, CA (US)

( * ) Notice: Subject to any disclaimer, the term of this patent is extended or adjusted under 35 U.S.C. 154(b) by 36 days.

(21) Appl. No.: 14/180,974

(22) Filed: Feb. 14, 2014

(65) Prior Publication Data

US 2014/0226131 A1    Aug. 14, 2014

Related U.S. Application Data

(60) Provisional application No. 61/764,939, filed on Feb. 14, 2013.

(51) Int. Cl.
*A61B 3/113* (2006.01)
*G06F 1/16* (2006.01)
(Continued)

(52) U.S. Cl.
CPC ............ *A61B 3/113* (2013.01); *G06F 1/1626* (2013.01); *G06F 1/1632* (2013.01); *G06F 3/013* (2013.01);
(Continued)

(58) Field of Classification Search
None
See application file for complete search history.

(56) References Cited

U.S. PATENT DOCUMENTS 7,986,816 B1\* 7/2011 Hoanca ............. G06K 9/00597
382/115
2005/0175218 A1    8/2005 Vertegaal et al.
(Continued)

FOREIGN PATENT DOCUMENTS

CN    102221883 A    10/2011
CN    105247447 A    1/2016
(Continued)

OTHER PUBLICATIONS

Blignaut. Pieter, et al., "TrackStick: a data quality measuring tool for Tobii eye trackers", Proceedings of the Symposium on Eye Tracking Research and Applications, (2012), 293-296.
(Continued)

*Primary Examiner* — Carolyn R Edwards
*Assistant Examiner* — Krishna Neupane
(74) *Attorney, Agent, or Firm* — Fenwick & West LLP

(57) ABSTRACT

Methods and systems to facilitate eye tracking control calibration are provided. One or more objects are displayed on a display of a device, where the one or more objects are associated with a function unrelated to a calculation of one or more calibration parameters. The one or more calibration parameters relate to a calibration of a calculation of gaze information of a user of the device, where the gaze information indicates where the user is looking. While the one or more objects are displayed, eye movement information associated with the user is determined, which indicates eye movement of one or more eye features associated with at least one eye of the user. The eye movement information is associated with a first object location of the one or more objects. The one or more calibration parameters are calculated based on the first object location being associated with the eye movement information.

12 Claims, 11 Drawing Sheets

(51) Int. Cl.
G06F 3/01 (2006.01)
G06F 3/038 (2013.01)
G06F 21/36 (2013.01)
G06K 9/00 (2006.01)

(52) U.S. Cl.
CPC ............ *G06F 3/038* (2013.01); *G06F 21/36* (2013.01); *G06K 9/00604* (2013.01)

(56) References Cited

U.S. PATENT DOCUMENTS

| | | | |
|---|---|---|---|
| 2006/0227116 | A1 | 10/2006 | Zotov et al. |
| 2011/0254865 | A1 | 10/2011 | Yee et al. |
| 2011/0310006 | A1* | 12/2011 | Edwards ............... A61B 3/113 345/156 |
| 2012/0019662 | A1* | 1/2012 | Maltz ..................... G06F 3/013 348/158 |
| 2012/0272179 | A1 | 10/2012 | Stafford |
| 2014/0085198 | A1 | 3/2014 | Jahnke et al. |
| 2015/0084864 | A1* | 3/2015 | Geiss ..................... G06F 3/013 345/158 |
| 2016/0011658 | A1 | 1/2016 | Lopez et al. |
| 2016/0139665 | A1 | 5/2016 | Lopez et al. |

FOREIGN PATENT DOCUMENTS

| | | |
|---|---|---|
| EP | 2956844 A2 | 12/2015 |
| WO | WO-0133323 A2 | 5/2001 |
| WO | WO-2012052061 A1 | 4/2012 |
| WO | WO-2014125380 A2 | 8/2014 |
| WO | WO-2015154882 A1 | 10/2015 |
| WO | WO-2016075532 A1 | 5/2016 |

OTHER PUBLICATIONS

Santella, Anthony, et al., "Robust Clustering of Eye Movement Recordings for Quantification of Visual Interest", Symposium on Eye Tracking Research and Applications, (2004), 1-8.
"International Application Serial No. PCT/EP2015/000755, International Search Report mailed Jun. 9, 2015", 4 pgs.
"International Application Serial No. PCT/EP2015/000755, Written Opinion mailed Jun. 9, 2015", 8 pgs.
"Tobii—the workd leader in eye tracking", Tobii AB, [Online]. Retrieved from the Internet: <URL: http://www.tobii.com/>, (Accessed Oct. 1, 2015), 2 pgs.
Borah, Joshua, "Eye movement, measurement techniques for introduction", Encyclopedia of Medical Devices and Instrumentation, Second Edition, XP055196246, ISBN: 978-0-47-126358-6, Retrieved from the Internet: <http://onlinelibrary.wiley.com/store/10.1002/0471732877.emdll2/asset/emdll2.pdf?v=l&t=iazepui9&s=e27c8b48342ad445e2821290a3c8456408694987>, (Apr. 14, 2006), 263-286.
Fehringer, Benedict, et al., "Analysing the Potential of Adapting Head-Mounted Eye Tracker Calibration to a New User", International Symposium on Eye Tracking Research and Applications (ETRA), (2012), 4 pgs.
Jacob, Robert, "Eye Tracking in Advanced interface Design", (2003), 53 pgs.
Ramanauskas, N, "Calibration of Video-Oculographical Eye-Tracking System", Electronics and Electrical Engineering. No. 8(72), (2006), 65-68.
Yin, Shibin, et al., "A Vision-Based Self-Calibration Method for Robotic Visual Inspection Systems", Journal of Sensors 13(12), (2013), 16565-16582.
Zoccolan, Davide, et al., "A Self-Calibrating, Camera-based Eye Tracker for the Recording of Rodent Eye Movements", Frontiers in Neuroscience. vol. 4, Article 193, (Nov. 29, 2010), 1-12.
"DynaVox Announces the EyeMax: New Eye Gaze System Provides Greater Independence", [Online]. Retrieved from the Internet: <URL: http://www.dynavoxtech.com/company/press/release/detail.aspx?id=11>, (Aug. 6, 2008), 2 pgs.
"International Application Serial No. PCT/IB2014/000772, International Preliminary Report on Patentability mailed May 22, 2015", 30 pgs.
"International Application Serial No. PCT/IB2014/000772, International Search Report mailed Aug. 13, 2014", 4 pgs.
"International Application Serial No. PCT/IB2014/000772, Written Opinion mailed Feb. 9, 2015", 9 pgs.
"International Application Serial No. PCT/IB2014/000772, Written Opinion mailed Aug. 13, 2014", 8 pgs.
"U.S. Appl. No. 14/683,831, Non-Final Office Action mailed Jul. 21, 2016", 11 pgs.
"Chinese Application Serial No. 201480020096.6, Preliminary Amendment filed Apr. 14, 2016", W/ English Claims, 22 pgs.
"European Application Serial No. 14732364.6, Office Action mailed Mar. 18, 2016", 3 pgs.
"European Application Serial No. 14732364.6, Response filed Jul. 15, 2016 to Office Action mailed Mar. 18, 2016", 22 pgs.
"International Application Serial No. PCT/IB2015/002218, International Search Report mailed Apr. 1, 2016", 4 pgs.
"International Application Serial No. PCT/IB2015/002218, Written Opinion mailed Apr. 1, 2016", 6 pgs.
State Intellectual Property Office of the People's Republic of China, First Office Action, Chinese Patent Application No. 201480020096.6, May 2, 2017, ten pages.

* cited by examiner

SYSTEMS AND METHODS OF EYE TRACKING CALIBRATION

CROSS-REFERENCE TO RELATED APPLICATIONS

This application claims a priority benefit of U.S. Provisional Application No. 61/764,939, filed Feb. 14, 2013, entitled "Systems and Methods of Eye Tracking Calibration," which is incorporated herein by reference in its entirety.

TECHNICAL FIELD

The present disclosure generally relates to eye tracking control and, more specifically, to systems and methods for facilitating eye tracking control calibration.

BACKGROUND

A gaze of a user may be determined using eye tracking technology that may be calibrated to the particular user whose gaze is being tracked. Calibration of eye tracking technology may include displaying calibration points on a display. A user may fixate on the calibration point, and the eye tracking technology may calibrate based on the known locations of the calibration points and eye information present through the images captured during the calibration processes.

An example of a calibration technique is described in U.S. Pat. No. 4,950,069 to Hutchinson, which describes a sequence of calibration points displayed at known locations on the display. The user fixates on each of the calibration points while the system collects information related to the user's pupil center and glint center. Once the calibration process is completed, the system computes the coefficients of a set of linear equations that map the pupil-glint displacement to the coordinates of the screen.

While such calibration techniques increase accuracy in eye tracking technology, they involve explicit involvement from the user, which may be cumbersome and time-consuming. Furthermore, if calibration is lost (e.g., due to changes in the illumination in the environment), the user will need to stop the current activity to rerun a calibration process in order to adjust the calibration parameters.

BRIEF DESCRIPTION OF THE DRAWINGS

Some embodiments are illustrated by way of example and not of limitation in the figures of the accompanying drawings.

DETAILED DESCRIPTION

Figure 1:
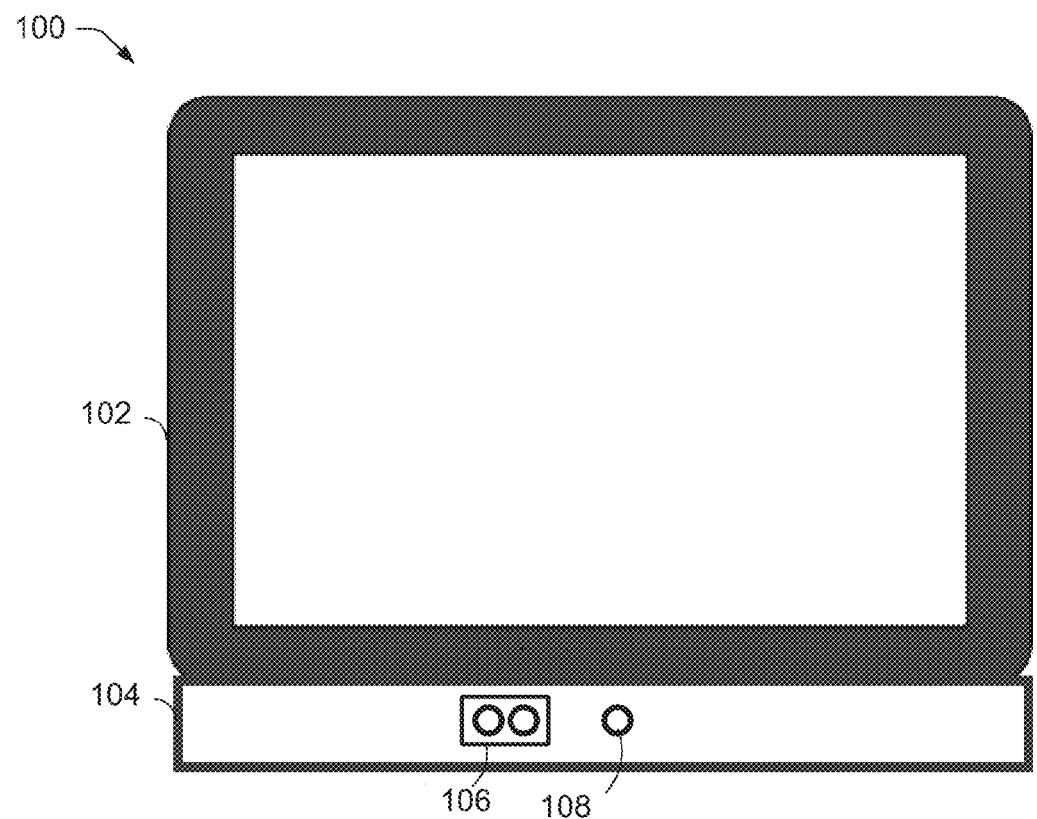
FIG. 1 is a device diagram of an example computing device coupled to a docking device capable of facilitating eye tracking control, according to some embodiments.

Example systems and methods to facilitate eye tracking control calibration are described. In the following description, for purposes of explanation, numerous specific details are set forth in order to provide a thorough understanding of example embodiments. It will be evident, however, to one skilled in the art that the present technology may be practiced without these specific details.

A user of a computing device may interact with and control objects and applications displayed on the computing device through the user's eye movement. An image of the user's eyes and/or face, captured by a camera on the computing device or on a device coupled to the computing device, may be analyzed using computer-vision algorithms, such as eye tracking and gaze detection algorithms. For example, the captured images may be processed to extract information relating to features of the user's eyes and/or face. The computing device may then use the extracted information to determine the location of the user's eyes and estimate the gaze information associated with the user. Gaze information of a user may be an estimation of where the user is looking and may include information such as a user's line of sight, point of regard information (e.g., a location on the display at which the user is looking), the direction of the user's gaze, and the like. For example, the computing device may be able to estimate at which icon on the display the user is looking. The estimation of where the user is looking may be used to direct one or more objects, applications, and the like to perform a particular operation. For example, the user may direct and control the movement of an object on the screen depending on where the user is looking on the display of the computing device, including controlling scrolling functions, the movement of objects in a virtual game, controlling the pointer and cursor position, and the like. The estimation of where the user is looking may also be used to analyze the areas or objects displayed on the screen that appear to attract the attention of the user, or the estimation may be used to study the objects a user looks at on a graphical user interface. For example, the design of an application user interface may be improved using eye tracking information indicating areas or objects attracting the users' attention so that users have a better experience when interacting with the application.

A calibration process may be conducted when the user begins using the computing device in order to calculate calibration parameters associated with the user. These calibration parameters may be taken into account to accurately determine the location of the user's eyes and estimate the location on the display at which the user is looking. The calibration parameters may also be taken into account to determine the direction of the user's eye gaze in three-dimensional (3-D) space (e.g., line of sight). The computing device may calibrate the eye control calculations by displaying a sequence of one or more display objects at known locations on the display and determining the location on the display at which the user is looking while adjusting for unique characteristics associated with the user. The calibration process may be performed in a manner such that the user is unaware that the calibration process is occurring. For example, the user may be playing a game that includes game objects displayed such that they appear to be moving on the display of the computing device. The game objects may be used to covertly calibrate the eye control calculations to more accurately reflect the user's eye characteristics. This calibration of the system may be continuous and may take place while the user is playing the game in a manner such that the calibration is undetectable by the user. In the case of an application not directly controlled by the user (e.g., collecting eye gaze data while a commercial is displayed on a screen), the calibration parameters might be calculated offline based on the eye movement patterns detected.

FIG. 1 is a device diagram 100 of an example computing device 102 coupled to a docking device 104 capable of facilitating eye tracking control. The computing device 102 may be any type of computing device, including, but not limited to, a smart phone, a personal digital assistant (PDA), a mobile phone, a computing tablet, an electronic reader, a television, a laptop, a desktop computer, a display device, a head-mounted display, and the like. During eye tracking control, the computing device 102 may be used by the user by holding the computing device 102 with one hand, both hands, or while the computing device 102 is on a stand or resting on a surface.

A docking device 104 may be coupled to the computing device 102 in any manner, such as through a universal serial bus (USB) port on the computing device 102, micro USB port on the computing device 102, and the like. While the docking device 104 of FIG. 1 is depicted at the bottom of the computing device 102, one of ordinary skill in the art will appreciate that the docking device 104 may be located at any suitable location relative to the computing device 102. The docking device 104 may include a camera module 108 and one or more light-emitting diodes (LEDs) 106. For explanatory purposes, LEDs 106 are depicted and described throughout the disclosure. However, one of ordinary skill in the art will appreciate that any appropriate light-emitting source may be used (e.g., infrared laser). Additionally, while one or more LEDs are depicted through the disclosure, one of ordinary skill in the art will appreciate that the eye tracking functionality may operate without LEDs.

The docking device 104 may include any number of infrared LEDs 106 that may be placed in a suitable location in any manner within the docking device 104 (e.g., tilted at an angle such that it points toward the user's face). In a specific embodiment, the one or more LEDs 106 may be synchronized with the one or more cameras in such a manner that the one or more LEDs are turned on when the one or more cameras are grabbing a frame, and turned off otherwise. In some embodiments, the LEDs may be turned off if no movement has been detected or if the docking device 104 and/or computing device 102 go into a sleep mode.

In some embodiments, the docking device 104 may also include a suitable type of infrared pass filter (e.g., active, mechanical, high-pass, band-pass, etc.). In some embodiments, a high-pass filter that blocks light below 800 nm and allows light above 800 nm is used. In some embodiments, the infrared band pass filter may only allow light between 800-900 nm to enter the one or more cameras of the camera module 108.

The camera module 108 may include one or more front-facing cameras placed in any suitable location in any manner within the docking device 104 (e.g., tilted at an angle such that it points toward the user's face) and may be used to capture images of the user's eyes and/or face. The one or more cameras may be placed at an appropriate distance from the LEDs 106 to optimize the proper capture of the infrared light. In some embodiments, a camera on the computing device 102 is used in combination with camera module 108 in stereo mode. In some embodiments, the camera module 108 may include any one or more of the following: a black and white (e.g., monochrome) or color (e.g., RGB) complementary metal-oxide-semiconductor (CMOS) sensor, running at an appropriate frame-per-second rate (e.g., high-definition at 30 frames per second), a lens without an infrared block filter and with an appropriate field of view (e.g., approximately 35 degrees) and depth of field (e.g., approximately 30-80 cm for a mobile device, and approximately 2-5 meters for a television), and the like. The one or more cameras in the camera module 108 may be positioned such that the one or more cameras are tilted toward a user's face.

The images captured by the camera may be rotated. The eye tracking software can use sensors on the computing device 102 (e.g., accelerometer, magnetometer, etc.) to detect the orientation of the computing device 102 and rotate the image accordingly so that it can be properly processed.

The LEDs 106 emit light that may be focused and centered toward the eyes of the user. The infrared light from the LEDs 106 is reflected in the pupil and on the cornea of the user and recorded by the cameras in the camera module 108. In some embodiments, the LEDs 106 may be synchronized with the one or more cameras so that the LEDs 106 are on only when the one or more cameras are grabbing an image. In some embodiments, to improve the image quality, the visible light below 800 nm is filtered out using an infrared pass filter. The field of view and depth of view of the lenses of the one or more cameras in the camera module 108 may allow the user to move around, thereby accommodating for head pose variance of the user. The eye tracking control software may analyze the images taken by the camera module 108 to provide screen coordinates (x, y) of where the user is looking on the display of the computing device 102. These coordinates may be used for any number of applications (e.g., scrolling, moving objects, selecting icons, playing games, etc.).

The LEDs 106 and the camera module 108 may be turned on and/or off in any manner, such as by utilizing an external slider, an on-off dedicated button on the side or on the back of either the computing device 102 or the docking device 104, controlled by an application or a digital button on the screen, controlled by movement or shaking of the computing device 102 and/or the docking device 104, controlled by voice commands, on-screen capacitive buttons, touch pad(s), bio-signals (e.g., EMG, EEG, etc.), remote control, hand and/or figure gestures, and the like. As such, in some embodiments, the eye tracking components may consume power only while the LEDs and the camera are turned on (e.g., when the user is using the eye tracking features).

In some embodiments, the eye tracking features are optimized when the camera is located at the bottom of the computing device 102 (e.g., with respect to the perspective of the user). The user may rotate the computing device 102 coupled to the docking device 104 to properly orient the camera module 108 such that it is located at the bottom of the computing device 102. In some embodiments, using the accelerometer and/or magnetometer of the computing device 102, the LEDs, the pass filter, and/or the camera may be turned on and/or off depending on the orientation of the computing device 102 and the docking device 104 (e.g., turn off the LEDs and the camera when the computing device 102 and the docking device 104 are rotated such that the camera module 108 is located at the top of the computing device 102 with respect to the perspective of the user).

The LEDs and the camera may be turned off when the user's face is not recognized for a predetermined amount of time (e.g., 5-10 seconds) and may turn on again when the user's face or parts of the user's face (e.g., the user's iris) is detected and recognized.

Figure 2:
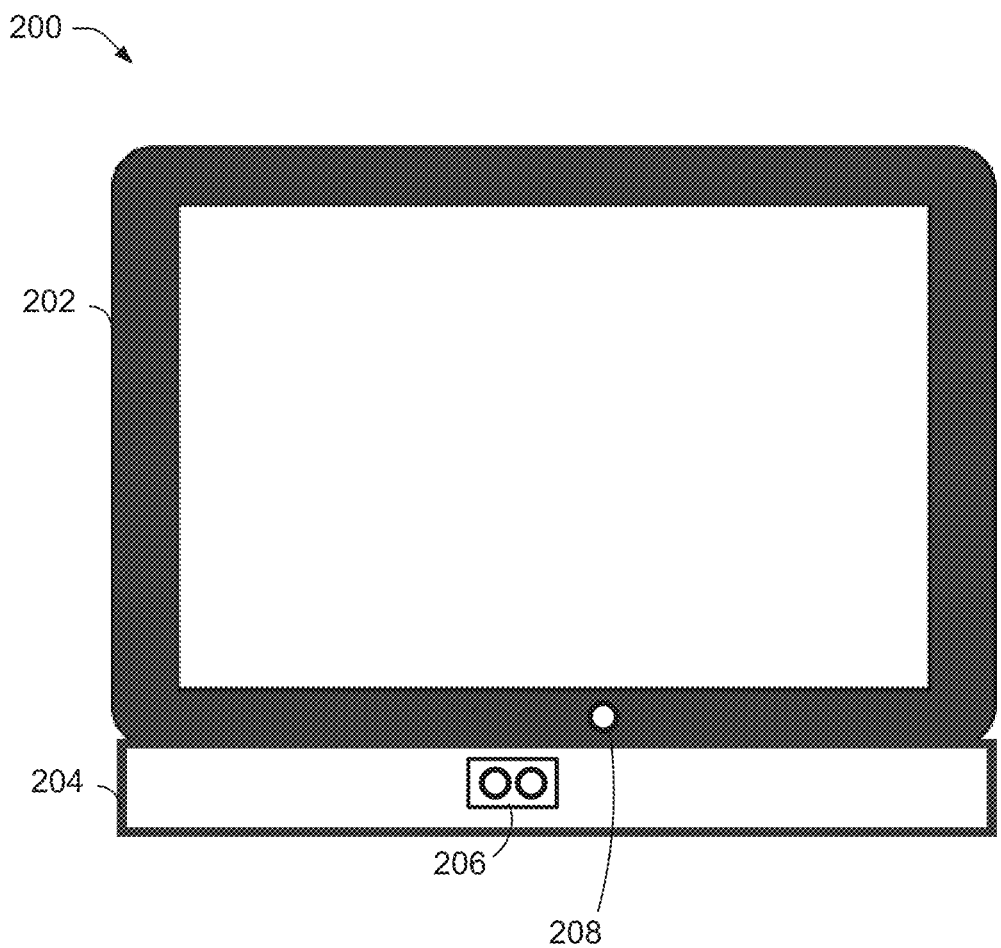
FIG. 2 is a device diagram of another example of a computing device coupled to a docking device capable of facilitating eye tracking control, according to some embodiments.

FIG. 2 is a device diagram 200 of another example of a computing device 202 coupled to a docking device 204 capable of facilitating eye tracking control. The example shown in FIG. 2 may operate similarly to the example shown in FIG. 1 and may incorporate any one or combination of features described for FIG. 1. However, FIG. 2 shows that the docking device 204 may be integrated with LEDs 206, and the camera module 208 of the computing device 202 may be used (instead of the camera module being integrated with the docking device 204). In some embodiments that couple the computing device 202 with the docking device 204 using a USB, a micro-USB port, or a proprietary port, the configuration depicted in FIG. 2 may allow for faster transfer of images from the camera since the camera of the computing device 202 is used to capture the images. The front-facing camera for eye tracking control may be utilized while simultaneously utilizing one or more back-facing cameras.

Figure 3A:
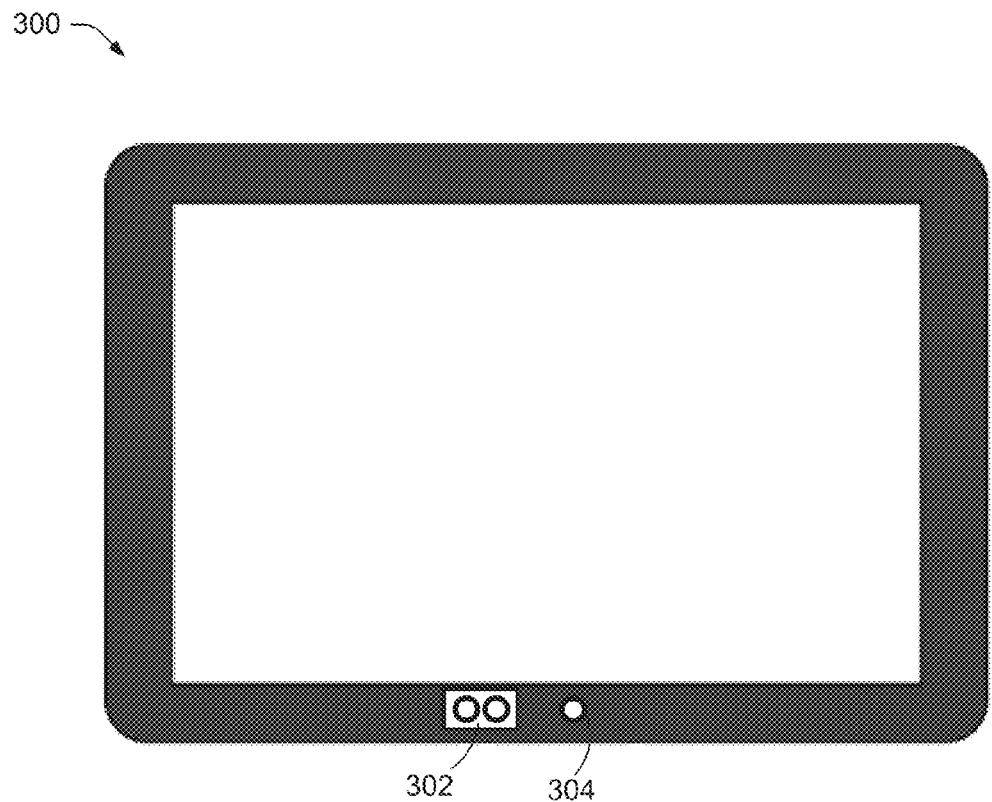
FIGS. 3A-3C are device diagrams of example computing devices capable of facilitating eye tracking control, according to some embodiments.
Figure 3B:
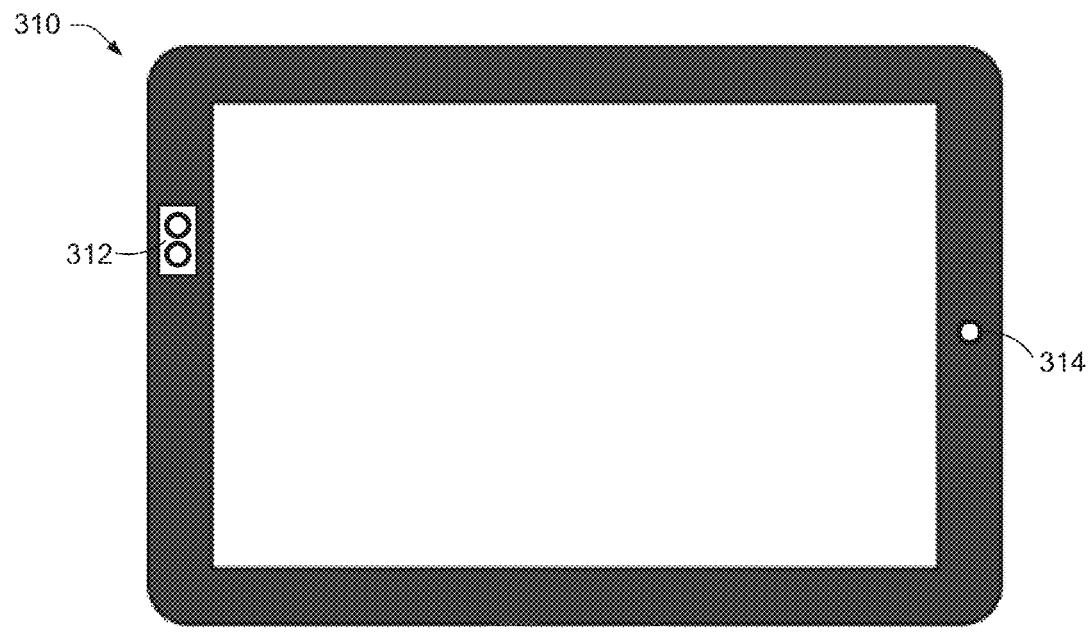
Figure 3C:
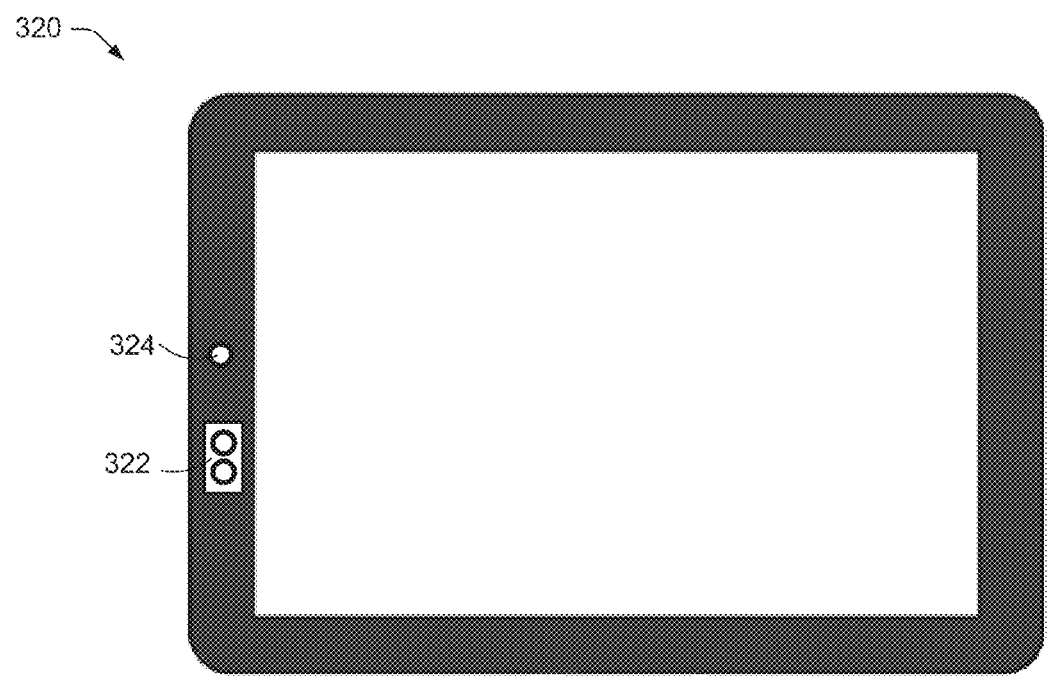

FIGS. 3A-3C are device diagrams of example computing devices capable of facilitating eye tracking control. The examples shown in FIGS. 3A-3C may operate similarly to the example shown in FIG. 1 and may incorporate any one or combination of features described for FIG. 1. However, the LEDs and camera modules are integrated into the computing device (instead of being part of a docking device). FIGS. 3A-3C depict computing devices 300, 310, 320, respectively, with LEDs 302, 312, 322 and camera modules 304, 314, 324 integrated into the computing devices 300, 310, and 320 in different example configurations (with respect to the user's perspective).

The LEDs 302, 312, 322 and the camera modules 304, 314, 324 on the computing devices 300, 310, 320 may be located in any one of a number of configurations on the computing devices. FIG. 3A shows the LEDs 302 and the camera module 304 being located at the bottom of the computing device 300. FIG. 3B shows the LEDs 312 being located on one side of the computing device 310 while the camera module 314 is located on the opposite side of the computing device 310. FIG. 3C shows the LEDs 322 and the camera module 324 being located on the same side of the computing device 320.

Figure 4:
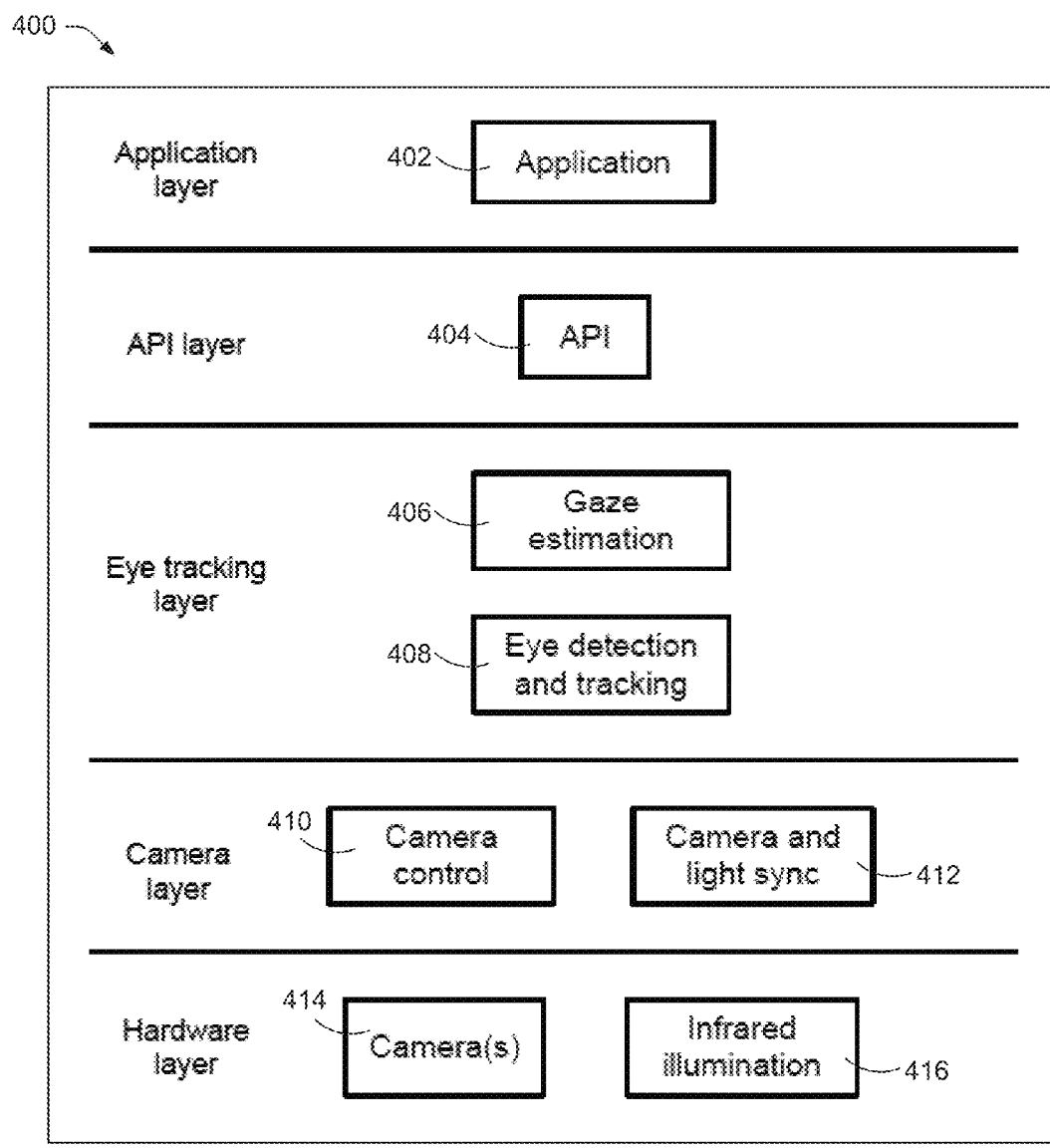
FIG. 4 is a block diagram of an example software architecture for facilitating eye tracking control, according to some embodiments.

FIG. 4 is a block diagram of an example software architecture 400 for facilitating eye tracking control. Any one or more of the components of the software architecture 400 may run on either a control processing unit (CPU) of the computing device or on a combination of a CPU and a graphics processing unit (GPU) of the computing device. In some embodiments, any one or more of the components of the software architecture 400 may run on a dedicated chip. The software may run as a background process (e.g. as part of the operating system (OS), in a web browser, etc.) and may provide an application programming interface (API) that other applications can access. The API may raise an event or use some other similar mechanism to send the information of where the user is looking on the screen to other applications.

The software architecture 400 may be divided into different layers. The bottom layer may include a camera module 414 and an infrared illumination module 416 that may correspond to the respective hardware (e.g. the camera(s), the infrared illumination, etc.). A camera layer may include a camera control module 410 that may be in charge of communicating with the camera(s) in order to perform camera operations such as, for example, starting the camera, grabbing images, controlling the camera properties, and the like. This layer may also include a camera and light sync module 412, which may synchronize the one or more cameras and the infrared emitters so that the lights are turned on by the eye tracking software in order to improve tracking of the user's eyes and minimize energy consumption. In some embodiments, the eye tracking algorithms may be used to optimize the infrared illumination by decreasing or increasing the amount of light depending on parameters issued by the eye tracking engine. In some embodiments, the camera layer may be configured to strobe the infrared LEDs at the frequency of the camera trigger output.

The camera layer may deliver images to the eye tracking layer or eye tracking engine. In the eye tracking layer, a gaze estimation module 406 may process images to find features like face location, eye region location, pupil center, pupil size, location of the corneal reflections, eye corners, iris center, iris size, and the like. These features may be used by the eye detection and tracking module 408 in the gaze estimation stage, which may be in charge of calculating the point of regard of the user, which may be the location on the display where the user is looking. The gaze estimation module 406 may also calculate the optical and visual axes of the user's eyes and calibrate the calculation based on specific features of the user.

The API layer may be used for communication between the eye tracking layer and applications that use eye gaze information (e.g., OS API, games that employ eye gaze information, etc.). An API module 404 may send data calculated by the eye tracking layer, such as coordinates of the point of regard, three-dimensional (3D) location of the user's eyes, pupil size, distance between the eyes, head orientation, head movement, and the like. The API module 404 may also accept commands from an application to the eye tracking layer (e.g., to start and/or stop the eye tracking engine, query for specific information, etc.). An application module 402 may connect to the eye tracker's API module 404 and use eye gaze information for any suitable purpose (e.g., control an app or a game, record eye data for visual behavior studies, etc.).

Figure 5:
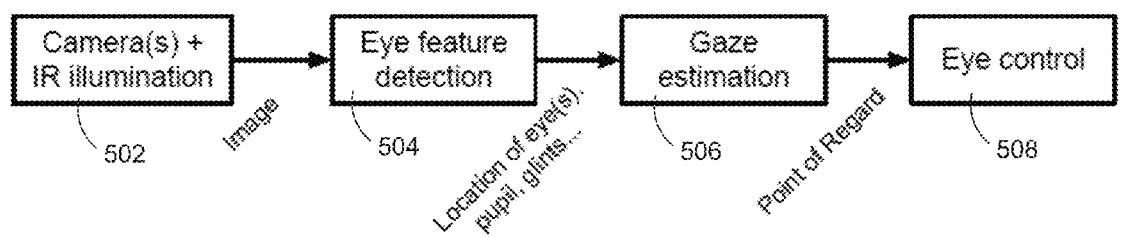
FIG. 5 is a block diagram of an example flow of data used to facilitate eye tracking control, according to some embodiments.

FIG. 5 is a block diagram of an example flow of data used to facilitate eye tracking control. The one or more cameras and the infrared LED illumination modules 502 may capture an image of the user. The eye feature detection module 504 may use the captured data to detect eye features (e.g., location of eye(s), pupil(s), iris(es), corneal reflections, etc.). Using the detected eye features, the gaze estimation module 506 may estimate the user's point of regard and/or line of sight, which may then be used to control aspects of an application through the eye control module 508.

A calibration process may be conducted when the user initially uses the eye tracking functionality in order to calculate calibration parameters specific to the user (e.g., vertical and horizontal offset between optical and visual axes) and/or to calculate parameters of a mapping function that may map eye features on the image coordinate system to the screen coordinate system. These calibration parameters and the information of the face and eyes are then employed to estimate where the user is looking on the screen through a gaze estimation algorithm. Any suitable calibration process may be used to calculate the calibration parameters specific to the user.

In some embodiments, the eye tracking system may be calibrated (or recalibrated) by matching a path followed by a moving target displayed on a display of the computing device with a path described by any eye information such as the pupil, the iris, the point of regard, the optical axis, the visual axis, the one or more corneal reflections produced by the one or more infrared light sources, or a combination of these.

In some embodiments, an application that uses eye tracking information may display a sequence of static or moving objects unrelated to a calibration process in different locations of the screen. For example, a game may display a sequence of graphical objects during an initial stage of the game (e.g., a sequence of enemies). The user may look at the displayed graphical objects and may interact with them (e.g., by pressing a button to shoot at the objects). While the user plays this stage of the game, the application may collect eye information and calculate the calibration parameters, where such processes are undetectable to the user. Once the one or more calibration parameters have been determined, the system may compute gaze data associated with the user, including the point of regard indicating the location of the screen at which the user is looking and/or the line of sight indicating the direction of the user's gaze in 3D space. At any point, the application may send coordinates corresponding to onscreen locations of graphical objects to the eye tracking engine in order to validate and/or update the calibration parameters. In some embodiments, the application may identify a portion of the screen where one or more calibration parameters are inaccurate and may display objects in the area that may be used to adjust the one or more calibration parameters.

In some embodiments, an application may present one or more objects as text displayed at known locations, and the text may be used for calibration. For example, a set of instructions may be displayed on the screen describing how to use the eye tracking software. While the user reads the text of the instructions, the eye information associated with the user may be collected by the eye tracking system. The eye tracking system may determine when the user is reading the text from the eye information collected. The text in the instructions may appear sequentially as the user reads to help the system determine what text the user is reading at any given time. The eye information collected may be associated with the location of the text and used to compute the calibration parameters such that the eye tracking software will be calibrated for the user once the user has finished reading the text.

In some embodiments, a user may be prompted to read and input different information during the initial setup process of a new device (e.g., a tablet, a smartphone, a PC, a TV, etc.). Examples of this may include reading information related to the device, setting the time zone of the device, setting up a network, entering the user's name, setting up a profile, advancing to the next page, and the like. The system may collect eye information while the user undergoes this process and match selected events (e.g. user selection of specific elements on the screen) to fixations taking place during a time window before the event occurs. The eye information collected in such way may be used to compute the calibration parameters such that the eye tracking software will be calibrated once the setup process is completed.

In some embodiments, one or more objects (e.g., numbers of a personal identification number (PIN) on a mobile device, objects and/or characters in a game, etc.) may be displayed on the display of the computing device such that they appear to be moving on a path with constant or variable velocity, which at some point reaches a value that is greater than zero. The user may look at one of the objects being displayed and follow that object with the user's eyes. The calibration parameters for the user may be computed by matching the path of that object with the path described by the user's eyes or, if the system has already been calibrated, the calculated point of regard, the visual axis, the optical axis, or any combination of these. If there is uncertainty between two or more objects, the application may modify the path and/or the velocity of those objects to determine at which object the user is looking. In some embodiments, the calibration process may occur in a manner such that the user may be unaware that the process is occurring. In some embodiments, the calibration process may run continuously in the background to continuously improve the calibration quality.

At any given point in time, a user interface may contain a set of N number of objects $O_i$ (where $i=1 \ldots N$) that move on a path $P_i$ with velocity $V_i$. The paths and velocities may change over time. For each frame captured by the one or more cameras, the system may match the path $P_i$ and velocity $V_i$ with the path E and velocity $V_e$ of one or both of the eyes of the user on a window of size W. The path E and the velocity $V_e$ may be calculated based on the location and movement of one or more eye features (e.g., the pupils, the irises, the one or more corneal reflections, and the like). If the system has been previously calibrated, the path E and the velocity $V_e$ may be calculated based on the point of regard, the optical axis, the visual axis, or any other appropriate factor. The comparison may be carried out by measuring the similarity of $P_i$ and $V_i$ with E and $V_e$ over the last W frames. Coordinates of objects may be normalized so they are in the same coordinate system.

The matching algorithm may calculate a matching coefficient $M_i$ that indicates the degree of similarity between the path of the object $P_i$ and the path of one or both eyes E. In some embodiments, the matching coefficient may be the Pearson product-moment correlation coefficient. If the matching coefficient $M_i$ is above a threshold T, the trajectories are considered to match.

For each comparison, multiple objects may have a matching coefficient above the threshold. The system may either ignore that comparison and continue to the next frame or may modify the path and/or velocity of the objects in dispute (and perhaps other objects as well) to ensure correct matching over the next frames.

For instance, consider a login screen on a mobile device that presents the numbers 0 to 9. Typically, a user may have to type in the correct digits of the user's PIN in order to unlock the device. However, using the eye tracking system, the user may look at each of the numbers of the PIN. In some embodiments, the numbers may move in different directions and at different velocities. For each new image captured by the camera, the system compares the trajectories of the numbers with the trajectory followed by the eyes (e.g. pupil centers). When more than one of the digits has a matching coefficient above the threshold, the system may modify the trajectories of those objects (and perhaps other objects as well) in a way that ensures correct matching. In this particular application, since the system knows which digit the user should be looking at in order to unlock the device, the modification of the path/velocity may be done in a way that maximizes the matching coefficient for that digit. If the correct digit is identified as the matching one, the system proceeds to the next digit (or unlocks the device if it was the last digit).

In another embodiment, the algorithm may run in the background while the user plays a game where characters and objects move on the screen. For every new frame, the system calculates the similarity of the paths followed by the objects displayed on the screen and the path followed by one or both eyes or point of regard (if the system is already calibrated). When the system finds a match, it uses the eye information of the images that produced the match to recalculate the calibration parameters. This process happens in the background and is invisible to the user and helps improve accuracy over time. The game may detect that a full recalibration is necessary, in which case the game may insert a sequence of events that are suited to recalibrate the system in such a way that the process is invisible for the user.

In another embodiment, the user may look at a commercial displayed on a screen (e.g. a tablet or a computer monitor) in a supermarket checkout line. The commercial may contain elements that move on the screen in different directions. The system calculates the similarity between the path and velocity of the objects and the path and velocity of the one or both eyes and finds a match. The system uses eye information collected when the match takes place to calibrate the system. Once the system is calibrated, it may inform the user, who may then use his or her eyes to interact with the information displayed on the screen. In some embodiments, the calibration process may be conducted after the commercial has been shown, and the calibration parameters may be computed in the cloud. This may be performed by creating a commercial that contains moving elements that can then be matched with the eye movement patterns of a user.

Figure 6A:
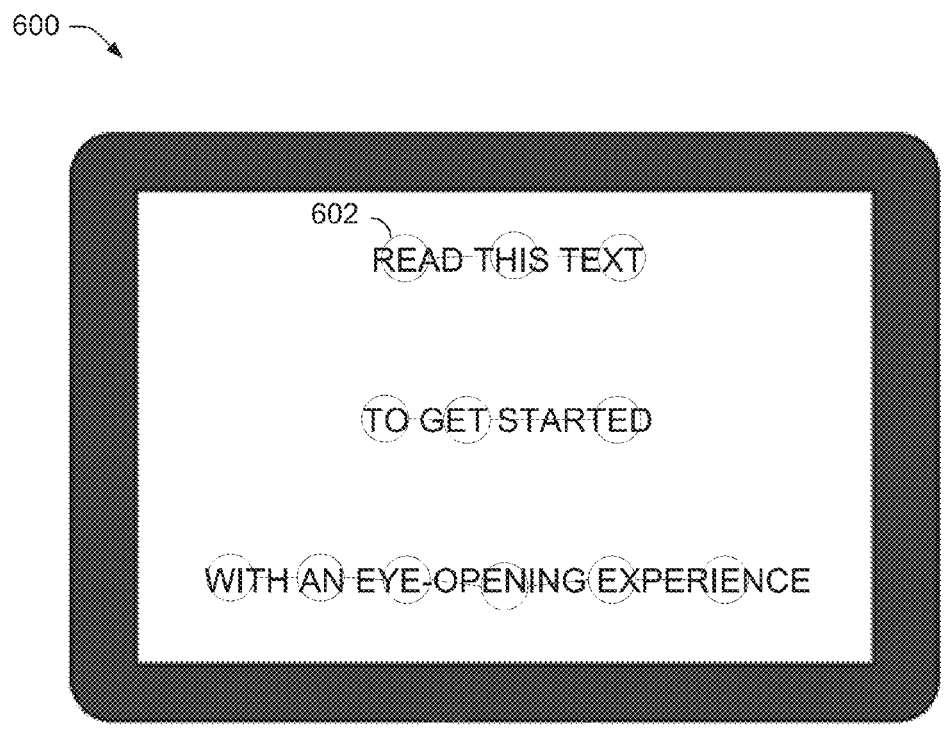
FIGS. 6A-6C are interface diagrams depicting example user interfaces displaying objects to facilitate eye tracking calibration, according to some embodiments.
Figure 6B:
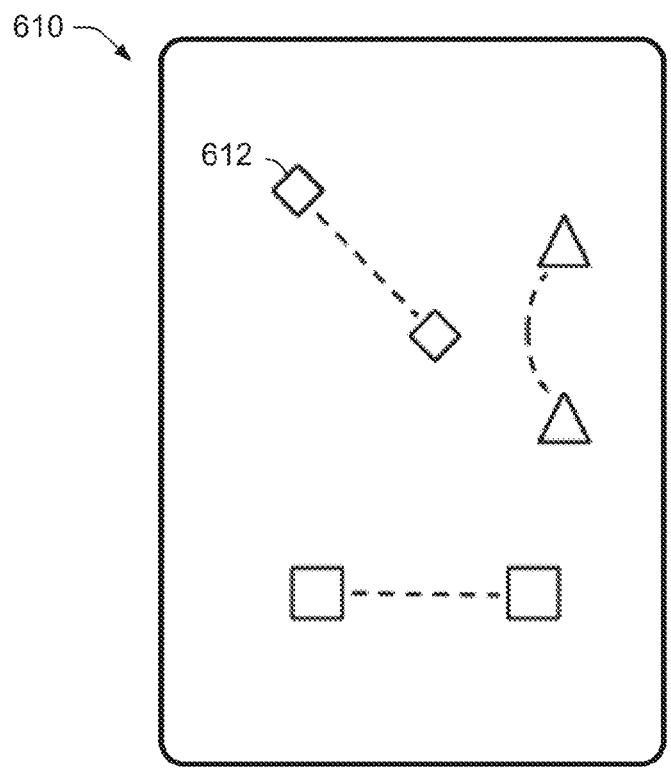
Figure 6C:
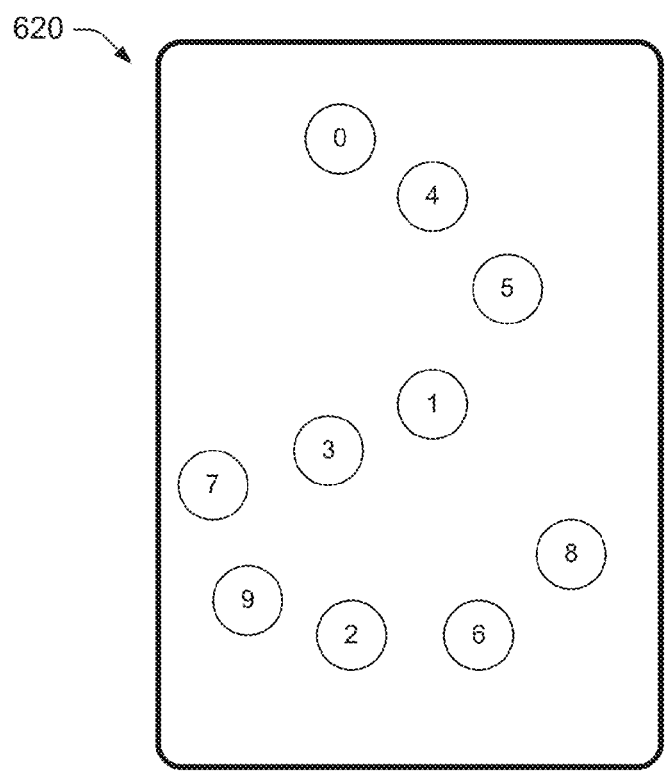

FIGS. 6A-6C are interface diagrams depicting example user interfaces 600, 610, and 620 displaying objects to facilitate eye tracking calibration. In FIG. 6A, the user interface 600 may display text that a user may read. The text may be in a known location of the user interface 600. The eye tracking system may match the sequence of eye movements that take place when the user reads the text (e.g., the sequence of fixations and saccades) and may use the eye information collected to compute the one or more calibration parameters. For example, the eye tracking system may detect that the user's fixation is at location 602 when the user begins reading the word "READ" and may similarly detect this for each word in the text such that the eye tracking system may be calibrated accordingly.

The user interface 610 of FIG. 6B shows objects (e.g., object 612) moving in various directions each following a particular path. The objects may be objects in an application the user is accessing. For example, the objects may be game objects in a game the user is playing on a computing device. As the one or more objects move on the user interface 610, the eye tracking system may track the user's eye movements and collect eye information (e.g., information about the pupil, iris, corneal reflections, optical axis, visual axis, etc.). The eye tracking system may measure the similarity of the paths of the objects with the path of the user's eye features to determine at which object the user is looking. The eye information collected may be associated with the location of the object on the display to compute the one or more calibration parameters.

The user interface 620 of FIG. 6C shows objects 0 to 9 representing numbers that may be included in a user's PIN used to access computing device features, including unlocking the computing device, accessing an application on the computing device, and the like. Each of the objects 0 to 9 may move at any particular velocity to any particular direction. When the user wishes to enter a PIN, the user may look at and/or follow the object representing the first number in the PIN. If the user has gazed upon the correct first number, the user may be notified that the user may look at the next number in the PIN. The notification may be provided to the user in any form. For example, the computing device may vibrate when the user has looked at the correct number, a notification may be displayed on the user interface 620, and the like. In some embodiments, the objects 0 to 9 may change directions after each correct entry of a digit of the PIN. When the user has correctly entered the PIN by gazing upon the correct numbers, access may be granted. Additionally, the eye tracking system may be calibrated as the user enters the PIN.

The movement pattern of the objects may change dynamically to allow the system to unambiguously match the movement of the eye with the movement of the digit. When uniqueness is established, the system may identify an area of the screen for which it has not yet obtained calibration data and display the next digit in that area. By repeating this operation for a particular number of times, the system will have obtained enough calibration data to estimate eye gaze accurately and will have controlled the user identity with the same security as physically entering the PIN. Further, since the user does not type the digits with the hands, it may be difficult for an observer to guess the PIN. In some embodiments, access control may be further combined with iris and/or face recognition, thereby achieving a higher degree of certainty. In some embodiments, iris and/or face recognition may occur using the image that is used to track the user's eye movement, another camera of the computing device, and the like. In some embodiments, voice recognition may also be used to obtain access.

Figure 7:
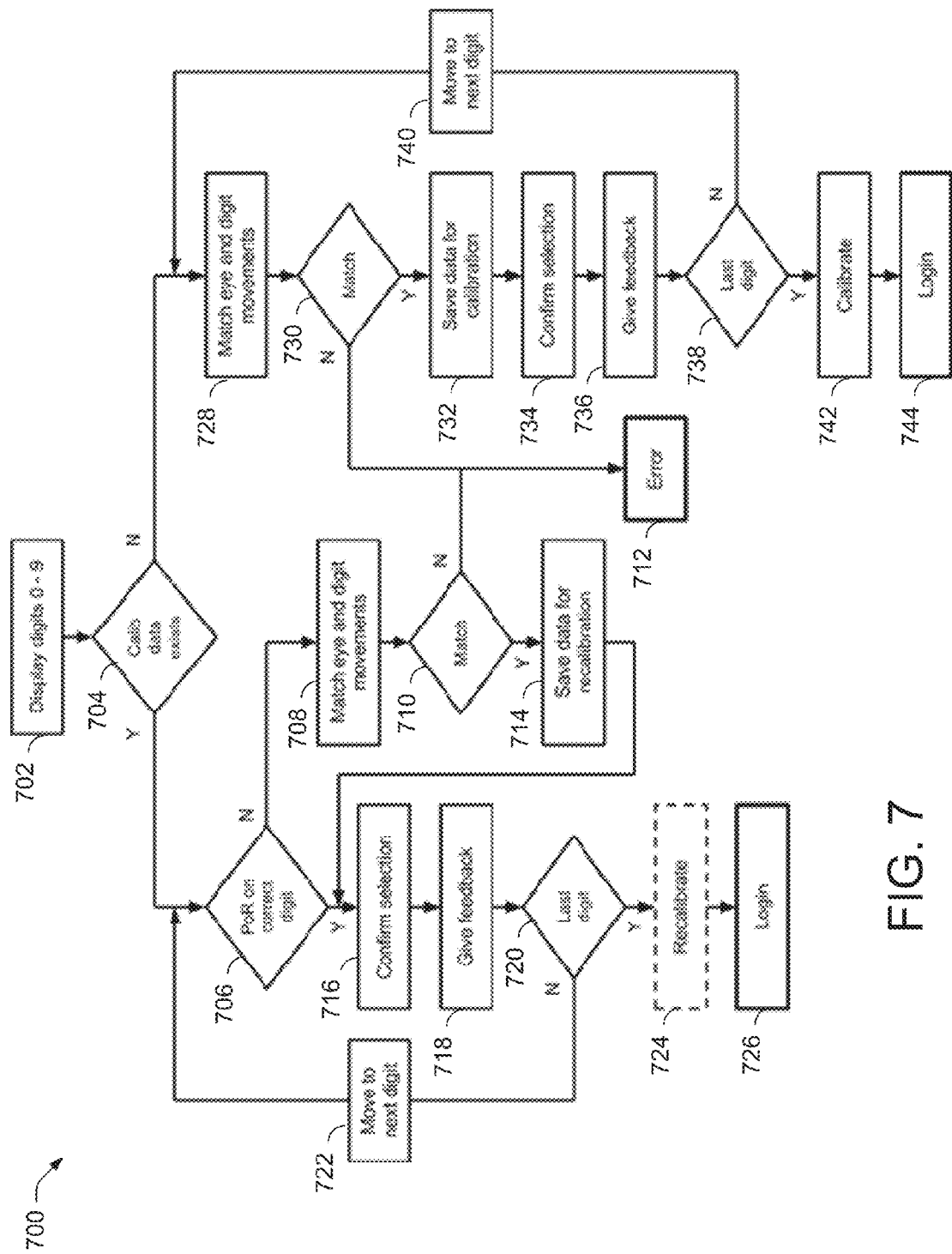
FIG. 7 is a flowchart of an example method of facilitating eye tracking calibration during personal identification number entry, according to some embodiments.

FIG. 7 is a flowchart of an example method 700 of facilitating eye tracking calibration during PIN entry. The method 700 may allow a user to unlock a computing device or an application on the computing device by looking at each digit of the set of digits that form a PIN of the user. The objects corresponding to numbers 0 to 9 may move on the screen in a seemingly random pattern. The system may include an eye tracking system that tracks the movements of the user's eye or eyes and matches the path of the eye movement with the path of the character the user is looking at. In some embodiments, this path can be changed dynamically to ensure a correct match. The eye tracking information captured during the screen unlock is used to calculate the user-specific calibration parameters of the gaze estimation subsystem.

In operation 702, the display digits 0 to 9 may be displayed on a display of the computing system. The digits may be displayed when a user is attempting to log into the user's computing device, an application on the computing device, and the like.

In operation 704, the eye tracking layer may determine whether calibration data exists for the user of the computing device.

In operation 706, if calibration data exists, the eye tracking layer determines whether the user's point of regard is located on the correct digit of the user's PIN.

In operation 708, if the user's point of regard is not on the correct digit, the eye tracking layer may match the user's eye movement with the movement of the corresponding digit that the user is looking at.

In operation 710, the eye tracking layer may determine whether the user's eye movement matches the movement of the corresponding digit.

In operation 712, if there is not a match between the user's eye movement and the movement of one of the digits being displayed, the eye tracking layer may return an error and may inform the user that the login was not successful.

In operation 714, if there is a match between the user's eye movement and the movement of a digit being displayed, then that data is saved for recalibration of the eye tracking system.

In operation 716, once the data is saved for recalibration, or if the user's point of regard is on the correct digit, the eye tracking layer may confirm whether the number gazed upon was the correct number to be entered for the PIN.

In operation 718, the eye tracking layer may return feedback to the user depending on whether the correct number in the PIN was gazed upon. The feedback may be any feedback that notifies the user that the digit gazed upon has been processed (e.g., vibration of the computing device, visual notification on the computing device, a sound, etc.).

In operation 720, the eye tracking layer determines whether the digit just processed was the last digit in the PIN.

In operation 722, if the digit just processed was not the last digit in the PIN, the eye tracking layer may move on to the next digit. In some embodiments, this includes changing the direction and velocity of the digits displayed in operation 702.

In operation 724, if the digit just processed was the last digit in the PIN, the eye tracking layer may recalibrate the eye tracking system based on data acquired from the matching of the user's eye movement to the digit movement.

In operation 726, the eye tracking layer may log the user into the computing device or to an application on the computing device.

In operation 728, if calibration data does not exist in operation 704, the eye tracking layer may match the user's eye movement with the corresponding digit based on the movement of the digit.

In operation 730, the eye tracking layer determines if there is a match between the user's eye movement and the movement of one of the digits being displayed. In operation 712, if there is no match, the eye tracking layer may return an error and may inform the user that the login was not successful.

In operation 732, if there is a match, the eye tracking layer may save the data acquired from matching the user's eye movement and the corresponding digit for calibration.

In operation 734, the eye tracking layer may confirm that the digit gazed upon by the user is the correct number in the PIN.

In operation 736, the eye tracking layer may return feedback to the user depending on whether the correct number in the PIN was gazed upon. The feedback may be any feedback that notifies the user that the digit gazed upon has been processed (e.g., vibration of the computing device, visual notification on the computing device, a sound, etc.).

In operation 738, the eye tracking layer may determine whether the digit just processed was the last digit in the PIN.

In operation 740, if the digit just processed was not the last digit in the PIN, the eye tracking layer may move on to the next digit. In some embodiments, this may include changing the direction and velocity of the digits displayed in operation 702.

In operation 742, if the digit just processed was the last digit in the PIN, the eye tracking layer may calibrate the eye tracking system based on data acquired from the matching of the user's eye movement to the digit movement.

In operation 744, the eye tracking later may log the user into the computing device or to an application on the computing device.

Figure 8A:
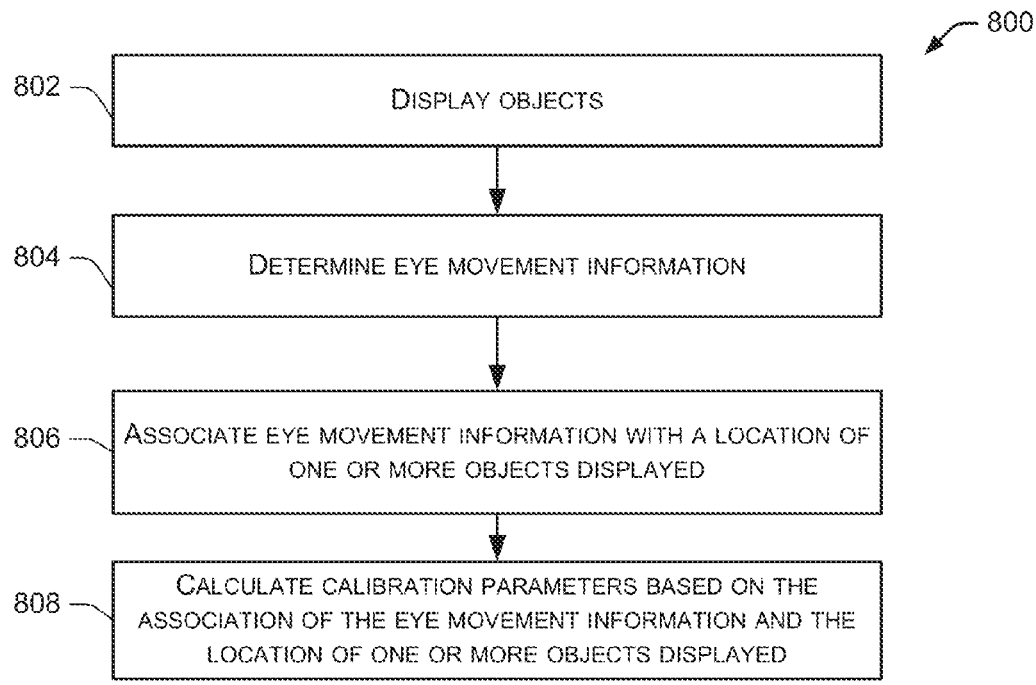
FIGS. 8A and 8B are flowcharts of example methods of facilitating eye tracking calibration, according to some embodiments.
Figure 8B:
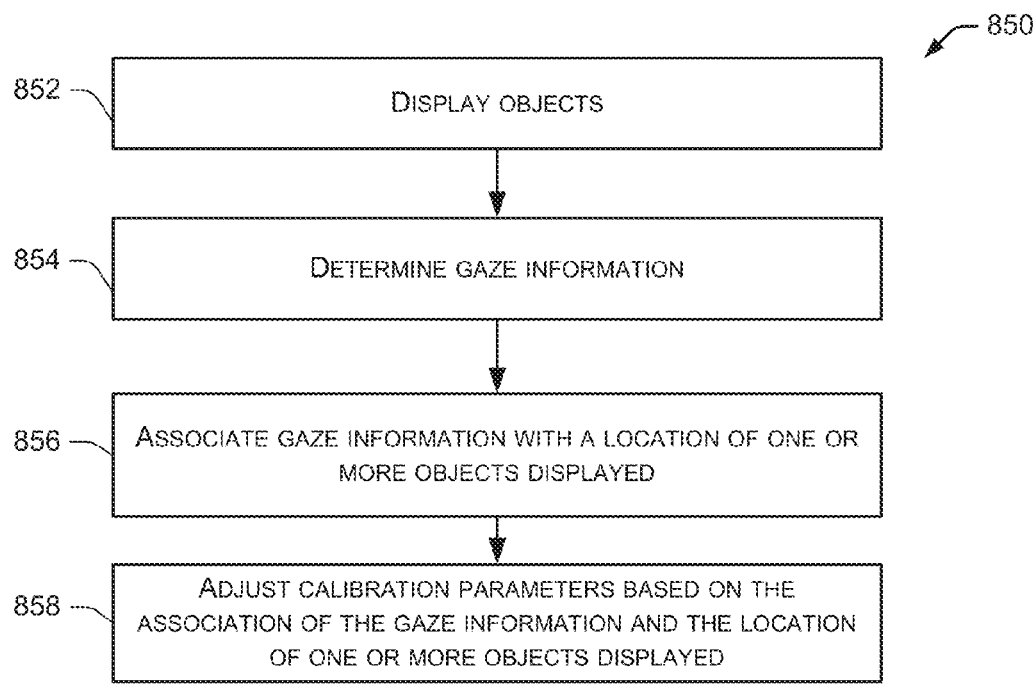

FIGS. 8A and 8B are flowcharts of example methods 800 and 850, respectively, of facilitating eye tracking calibration. The method 800 of FIG. 8A provides for calibration of an eye tracking system based on features and/or characteristics of a user by calculating one or more calibration parameters employed by the system to calculate the point of regard of the user, and the method 850 of FIG. 8B provides for recalibration of an eye tracking system that may have been previously calibrated for a user. While the examples of FIGS. 8A and 8B describe methods of calibration of a user, one of ordinary skill in the art will appreciate that the calibration methods may be used for more than one user using the eye tracking system at a given time.

In operation 802, a hardware-implemented display module displays objects on the display of the computing device of the user. The objects may be associated with a function unrelated to a calculation of eye movement information, calibration parameters, or gaze information (e.g., game functions, login functions, etc.).

In operation 804, a hardware-implemented eye tracking module may determine the eye movement information associated with the user. As described above, the eye movement information may include any information associated with the features and/or characteristics of the user (e.g., face location, eye region location, pupil center, pupil size, location of the corneal reflections, eye corners, iris center, iris size, iris patterns, eye movement patterns, etc.).

In operation 806, the hardware-implemented eye tracking module may associate the eye movement information with a location of one or more objects being displayed on the computing device. In some embodiments, the eye movement information may be associated with the location of an object as the object moves across the display. In some embodiments, the eye movement information may be associated with objects appearing at different locations on the display. In some embodiments, the eye movement information may be associated with static objects.

In operation 808, the hardware-implemented eye tracking module may calibrate (or recalibrate) the eye tracking system by calculating calibration parameters based on the association of the eye movement information and the location of the one or more objects displayed.

Once the eye tracking system is calibrated for the user, the eye tracking system may begin determining gaze information for the user based on the calibration parameters that are specific to the user (as calculated using the method 800 of FIG. 8A). FIG. 8B shows a method 850 of determining gaze information for the user.

In operation 852, a hardware-implemented display module displays objects on the display of the computing device of the user. The objects may be associated with a function unrelated to a calculation of eye movement information, calibration parameters, or gaze information (e.g., game functions, login functions, etc.).

In operation 854, a hardware-implemented eye tracking module may determine the gaze information associated with the user. As described above, the gaze information may indicate information associated with where the user is looking, which may include point of regard information, line of sight information, information about the direction of the user's gaze, and the like. The gaze information may be calculated using the calibration parameters calculated for the user.

In operation 856, the hardware-implemented eye tracking module may associate the gaze information with a location of one or more objects being displayed on the computing device. In some embodiments, the gaze information may be associated with the location of an object as the object moves across the display. In some embodiments, the gaze information may be associated with objects appearing at different locations on the display. In some embodiments, the gaze information may be associated with static objects.

In operation 858, the hardware-implemented eye tracking module may adjust the calibration parameters based on the association of the gaze information and the location of the one or more objects displayed.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., APIs).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 9:
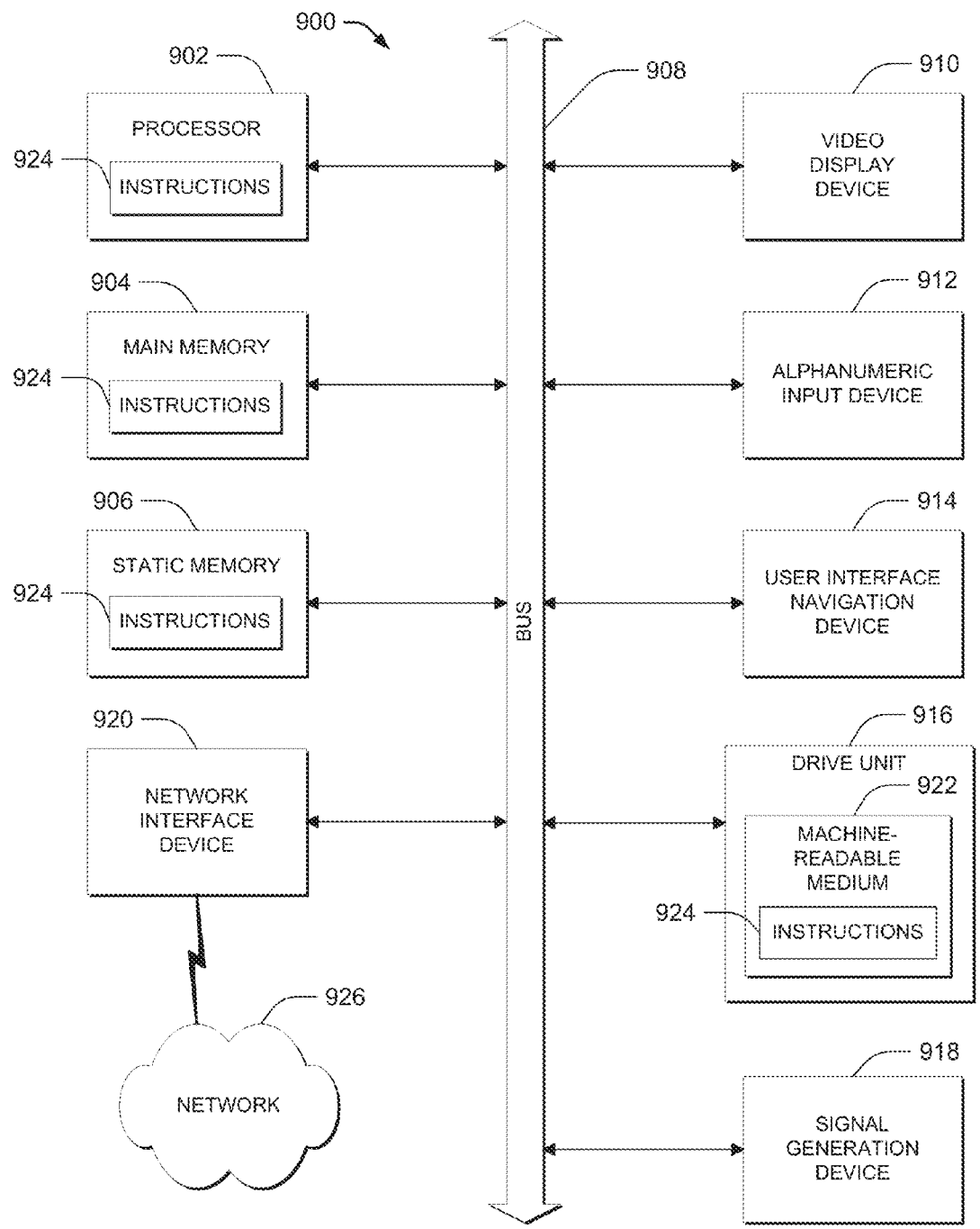
FIG. 9 is a block diagram of a machine in the example form of a computer system within which a set of instructions, for causing the machine to perform any one or more of the methodologies discussed herein, may be executed, according to some embodiments.

FIG. 9 is a block diagram of a machine in the example form of a computer system 900 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 900 includes a processor 902 (e.g., a CPU, a GPU, or both), a main memory 904, and a static memory 906, which communicate with each other via a bus 908. Computer system 900 may further include a video display device 910 (e.g., a liquid crystal display (LCD) or a cathode ray tube (CRT)). Computer system 900 also includes an alphanumeric input device 912 (e.g., a keyboard), a user interface (UI) navigation device 914 (e.g., a mouse or touch sensitive display), a disk drive unit 916, a signal generation device 918 (e.g., a speaker), and a network interface device 920.

Disk drive unit 916 includes a machine-readable medium 922 on which is stored one or more sets of instructions and data structures (e.g., software) 924 embodying or utilized by any one or more of the methodologies or functions described herein. Instructions 924 may also reside, completely or at least partially, within main memory 904, within static memory 906, and/or within processor 902 during execution thereof by computer system 900, with main memory 904 and processor 902 also constituting machine-readable media.

While machine-readable medium 922 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding, or carrying instructions for execution by the machine and that cause the machine to perform any one or more of the methodologies of the present technology, or that is capable of storing, encoding, or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Instructions 924 may further be transmitted or received over a communications network 926 using a transmission medium. Instructions 924 may be transmitted using network interface device 920 and any one of a number of well-known transfer protocols (e.g., HTTP). Examples of communication networks include a local area network (LAN), a wide area network (WAN), the Internet, mobile telephone networks, Plain Old Telephone (POTS) networks, and wireless data networks (e.g., WiFi and WiMAX networks). The term "transmission medium" shall be taken to include any intangible medium that is capable of storing, encoding or carrying instructions for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the technology. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
   displaying a first moving object on a display of a computing device, the first moving object moving along a first path;
   displaying a second moving object on the display of the computing device, the second moving object moving along a second path;
   capturing images of at least one eye of a user while the first moving object and the second moving object are displayed;
   while the first and second moving objects are displayed, determining, based on the images of the at least one eye captured while the first moving object and the second moving object are displayed, eye movement information associated with the user, the eye movement information indicating eye movement of one or more eye features associated with at least one eye of the user;
   determining which of the first path and the second path matches the eye movement information;
   associating the eye movement information with the matching path;
   calculating one or more calibration parameters for the user based on a location of the matching path and the eye movement information, the one or more calibration parameters relating to a calculation of gaze information of a user of the computing device;
   calculating gaze information based on the eye movement information and the one or more calibration parameters, the gaze information indicating information about where the user is looking;
   in response to the associating of the eye movement information with the matching path:
      changing the first path of the first moving object to a third path,
      changing the second path of the second moving object to a fourth path, and
      determining that the matching path corresponds to at least a portion of a login sequence of a user;
   after the changing of the first path and the second path, determining second eye movement information indicating second eye movement of the one or more eye features associated with the at least one eye of the user;
   determining which of the third path and the fourth path better matches the second eye movement of the one or more eye features associated with the at least one eye of the user;
   associating the second eye movement information with the determined path;
   determining that the determined path corresponds to a last portion in the login sequence of the user; and
   based on the determination that the determined path corresponds to the last portion in the login sequence of the user, granting access to an account of the user.

2. The method of claim 1, wherein the one or more calibration parameters comprise vertical offset or horizontal offset between optical and visual axes of the user.

3. The method of claim 1, further comprising:
   displaying a third object at a first location on the display;
   displaying a fourth object at a second location on the display after the third object is displayed at the first location;
   while the third object and the fourth object are displayed, determining the gaze information associated with the user;
   associating the gaze information with the first location and the second location; and
   adjusting the one or more calibration parameters based on the gaze information being associated with the first location and the second location.

4. The method of claim 1, further comprising:
   identifying a portion of the display of the computing device for which a calibration parameter of the one or more calibration parameters is inaccurate;
   displaying the first moving object within the portion of the display; and
   adjusting the one or more calibration parameters based on the first object movement being associated with the eye movement information.

5. The method of claim 4, further comprising:
   determining the gaze information based on the eye movement information and the one or more calibration parameters.

6. The method of claim 1, wherein:
   the determining of the eye movement information associated with the user includes:
      determining a path of the eye movement over a plurality of frames; and
      determining a velocity of the eye movement over a plurality of frames;
   the first moving object moves along the first path at a first velocity;
   the second moving object moves along the second path at a second velocity; and
   the determining which of the first path and the second path matches the eye movement information includes:
      measuring a similarity of the path of the eye movement to each of the first path and the second path; and
      measuring a similarity of the velocity of the eye movement to each of the first velocity and the second velocity.

7. A non-transitory machine-readable storage medium storing instructions which, when executed by one or more processors, cause the one or more processors to perform operations comprising:
   displaying a first moving object on a display of a computing device, the first moving object moving along a first path, displaying a second moving object on the display of the computing device, the second moving object moving along a second path;
   capturing images of at least one eye of a user while the first moving object and the second moving object are displayed;
   while the first and second moving objects are displayed, determining, based on the images of the at least one eye captured while the first moving object and the second moving object are displayed, eye movement information associated with the user, the eye movement information indicating eye movement of one or more eye features associated with at least one eye of the user;
   determining which of the first path and the second path better matches the eye movement of the one or more eye features associated with the at least one eye of the user;
   associating the eye movement information with the matching path;

calculating one or more calibration parameters for the user based on a location of the matching path and the eye movement information;

calculating gaze information based on the eye movement information and the one or more calibration parameters, the gaze information indicating information about where the user is looking;

in response to the associating of the eye movement information with the matching path:
  changing the first path of the first moving object to a third path;
  changing the second path of the second moving object to a fourth path; and
  determining that the matching path corresponds to at least a portion of a login sequence of a user;

after the changing of the first path and the second path, determining second eye movement information indicating second eye movement of the one or more eye features associated with the at least one eye of the user;

determining which of the third path and the fourth path better matches the second eye movement of the one or more eye features associated with the at least one eye of the user;

associating the second eye movement information with the determined path;

determining that the determined path corresponds to a last portion in the login sequence of the user; and based on the determination that the determined path corresponds to the last portion in the login sequence of the user, granting access to an account of the user.

8. The non-transitory machine-readable storage medium of claim 7, wherein the instructions cause the one or more processors to perform further operations, comprising:
  calculating the gaze information based on the eye movement information and the one or more calibration parameters.

9. The non-transitory machine-readable medium of claim 7, wherein:
  the determining of the eye movement information associated with the user includes:
    determining a path of the eye movement over a plurality of frames; and
    determining a velocity of the eye movement over a plurality of frames;
  the first moving object moves along the first path at a first velocity;
  the second moving object moves along the second path at a second velocity; and
  the determining which of the first path and the second path matches the eye movement information includes:
    measuring a similarity of the path of the eye movement to each of the first path and the second path; and
    measuring a similarity of the velocity of the eye movement to each of the first velocity and the second velocity.

10. A device, comprising:
  a hardware-implemented display module configured to:
    display a first moving object on a display of a computing device, the first moving object moving along a first path;
    display a second moving object on the display of the computing device, the second moving object moving along a second path; and
  a hardware-implemented eye tracking module configured to:
    capture images of at least one eye of a user while the first moving object and the second moving object are displayed;
    while the first and second moving objects are displayed, determine, based on the images of the at least one eye captured while the first moving object and the second moving object are displayed, eye movement information associated with the user, the eye movement information indicating eye movement of one or more eye features associated with at least one eye of the user;
    determine which of the first path and the second path better matches the eye movement of the one or more eye features associated with the at least one eye of the user;
    associate the eye movement information with the matching path;
    calculate one or more calibration parameters for the user based on a location of the matching path and the eye movement information;
    calculate gaze information based on the eye movement information and the one or more calibration parameters, the gaze information indicating information about where the user is looking;
    in response to the associating of the eye movement information with the matching path:
      change the first path of the first moving object to a third path;
      change the second path of the second moving object to a fourth path; and
      determine that the matching path corresponds to a digit in a PIN of a user;
    after the change of the first path and the second path, determine second eye movement information indicating second eye movement of the one or more eye features associated with the at least one eye of the user;
    determine which of the third path and the fourth path better matches the second eye movement of the one or more eye features associated with the at least one eye of the user;
    associate the second eye movement information with the determined path;
    determine that the determined path corresponds to a last digit in the PIN of the user; and
    based on the determination that the determined path corresponds to the last digit in the PIN of the user, grant access to an account of the user.

11. The device of claim 10, wherein the hardware-implemented eye tracking module is further configured to calculate the gaze information based on the eye movement information and the one or more calibration parameters.

12. The device of claim 10, wherein the hardware-implemented eye tracking module is further configured to:
  determine a path of the eye movement over a plurality of frames;
  determine a velocity of the eye movement over a plurality of frames;
  the first moving object moves along the first path at a first velocity;
  the second moving object moves along the second path at a second velocity; and
  the determination of which of the first path and the second path matches the eye movement information includes:
    measuring a similarity of the path of the eye movement to each of the first path and the second path; and measuring a similarity of the velocity of the eye movement to each of the first velocity and the second velocity.

* * * * *